US012629521B2

(12) United States Patent　　　　　(10) Patent No.:　US 12,629,521 B2
Gurfein et al.　　　　　　　　　　　　(45) Date of Patent:　May 19, 2026

(54) MICROCURRENT MIGRAINE TREATMENT DEVICE WITH AN ADAPTIVE TRIGGER

(71) Applicant: TIVIC HEALTH SYSTEMS INC., Menlo Park, CA (US)

(72) Inventors: Blake Taylor Gurfein, San Rafael, CA (US); John Claude, Redwood City, CA (US); Christopher A. Wiklof, Everett, WA (US)

(73) Assignee: Tivic Health Systems, Inc., San Antonio, TX (US)

( * ) Notice: Subject to any disclaimer, the term of this patent is extended or adjusted under 35 U.S.C. 154(b) by 286 days.

(21) Appl. No.: 18/365,623

(22) Filed: Aug. 4, 2023

(65) Prior Publication Data

US 2024/0066295 A1　　Feb. 29, 2024

Related U.S. Application Data

(63) Continuation of application No. PCT/US2022/029907, filed on May 18, 2022.

(60) Provisional application No. 63/189,948, filed on May 18, 2021.

(51) Int. Cl.
*A61N 1/36*　　　(2006.01)
*A61N 1/02*　　　(2006.01)
*A61N 1/04*　　　(2006.01)

(52) U.S. Cl.
CPC ......... *A61N 1/36031* (2017.08); *A61N 1/025* (2013.01); *A61N 1/0456* (2013.01); *A61N 1/36021* (2013.01); *A61N 1/36034* (2017.08)

(58) Field of Classification Search
CPC . A61N 1/36031; A61N 1/36034; A61N 1/025
USPC ............................................................. 607/45
See application file for complete search history.

(56) References Cited

U.S. PATENT DOCUMENTS

| 2009/0299432 | A1 | 12/2009 | Stadler et al. |
| 2012/0136408 | A1 | 5/2012 | Grill et al. |
| 2018/0207424 | A1* | 7/2018 | Mashiach .......... A61N 1/37235 |
| 2019/0217093 | A1* | 7/2019 | Claude .................... A61N 1/36 |

FOREIGN PATENT DOCUMENTS

| EP | 0 344 770 A1 | 6/1989 |

OTHER PUBLICATIONS

PCT International Search Report, dated Aug. 11, 2022, for PCT International Patent Application No. PCT/US2022/029907, filed May 18, 2022.
PCT Written Opinion of the International Searching Authority, dated Aug. 11, 2022, for PCT International Patent Application No. PCT/US2022/029907, filed May 18, 2022.

* cited by examiner

*Primary Examiner* — Nadia A Mahmood
(74) *Attorney, Agent, or Firm* — Launchpad IP, Inc.; Christopher A. Wiklof; James C. Larsen

(57)　　　　ABSTRACT

A microcurrent migraine treatment device includes an adaptive trigger circuit configured to dynamically determine a triggering threshold for applying a therapeutic microcurrent via a treatment electrode to a treatment location on a person's skin for treatment of a migraine condition.

26 Claims, 11 Drawing Sheets

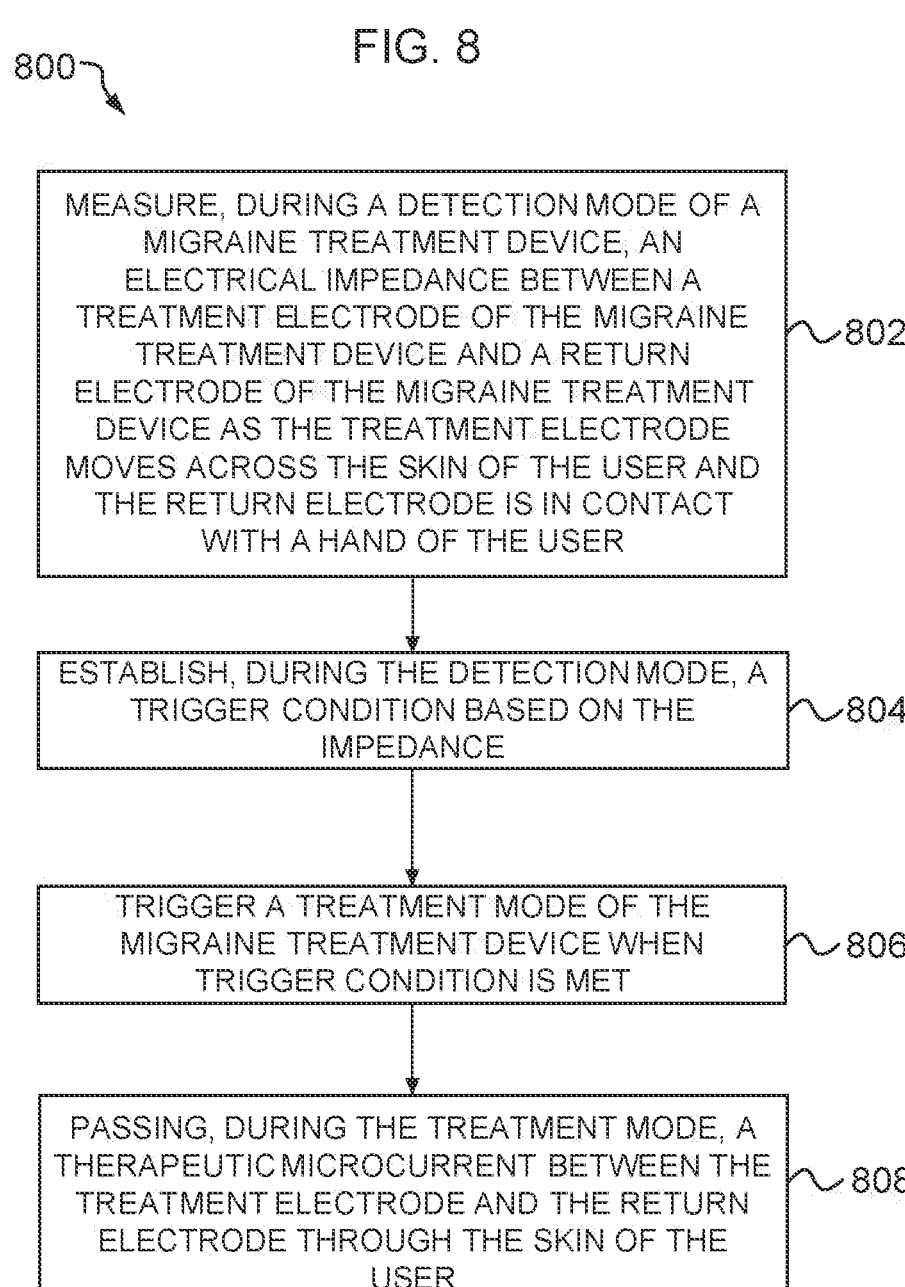

MEASURE, DURING A DETECTION MODE OF A MIGRAINE TREATMENT DEVICE, AN ELECTRICAL IMPEDANCE BETWEEN A TREATMENT ELECTRODE OF THE MIGRAINE TREATMENT DEVICE AND A RETURN ELECTRODE OF THE MIGRAINE TREATMENT DEVICE AS THE TREATMENT ELECTRODE MOVES ACROSS THE SKIN OF THE USER AND THE RETURN ELECTRODE IS IN CONTACT WITH A HAND OF THE USER ~802

ESTABLISH, DURING THE DETECTION MODE, A TRIGGER CONDITION BASED ON THE IMPEDANCE ~804

TRIGGER A TREATMENT MODE OF THE MIGRAINE TREATMENT DEVICE WHEN TRIGGER CONDITION IS MET ~806

PASSING, DURING THE TREATMENT MODE, A THERAPEUTIC MICROCURRENT BETWEEN THE TREATMENT ELECTRODE AND THE RETURN ELECTRODE THROUGH THE SKIN OF THE USER ~808

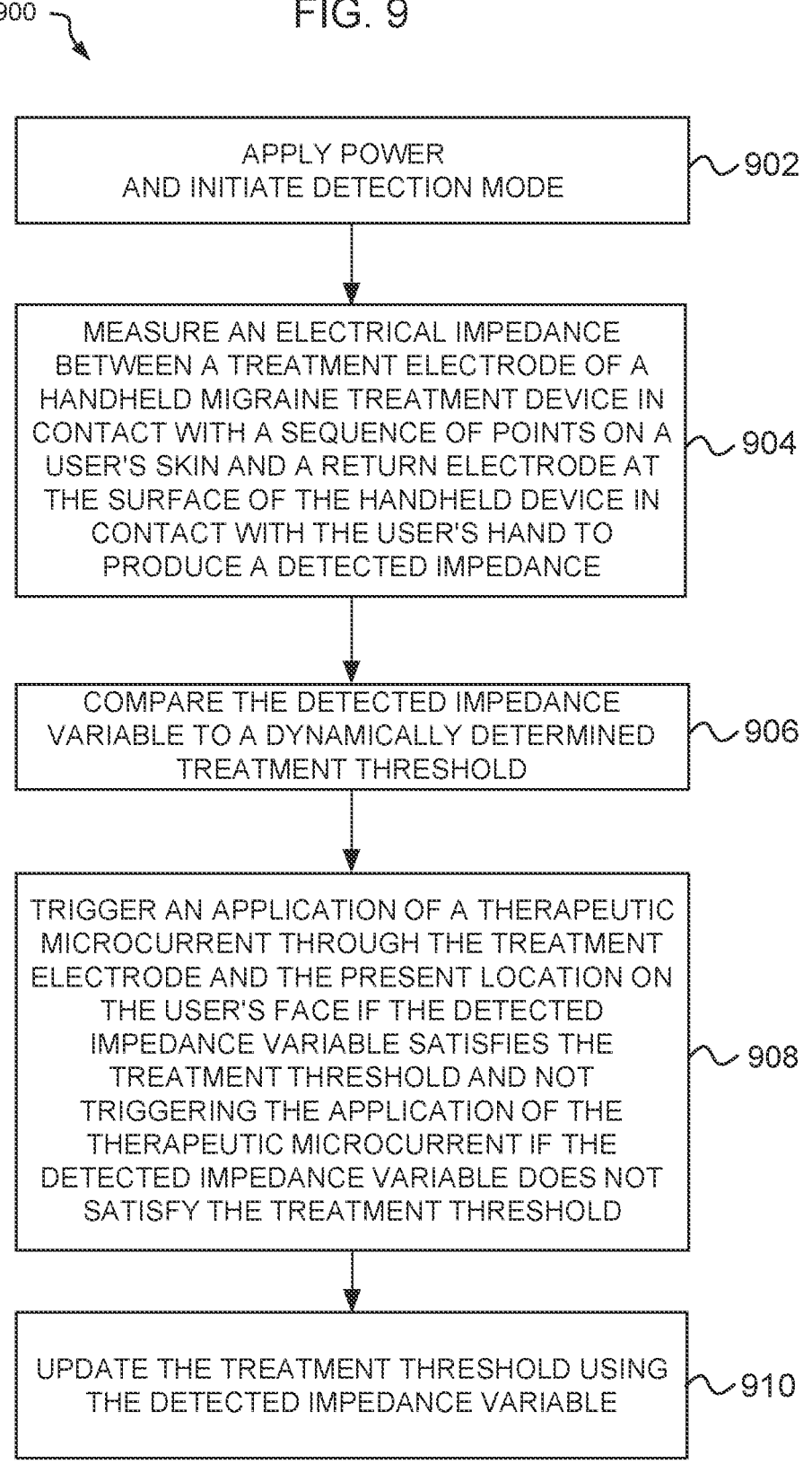

APPLY POWER
AND INITIATE DETECTION MODE                        ∿902

MEASURE AN ELECTRICAL IMPEDANCE
BETWEEN A TREATMENT ELECTRODE OF A
HANDHELD MIGRAINE TREATMENT DEVICE IN
CONTACT WITH A SEQUENCE OF POINTS ON A
USER'S SKIN AND A RETURN ELECTRODE AT          ∿904
THE SURFACE OF THE HANDHELD DEVICE IN
CONTACT WITH THE USER'S HAND TO
PRODUCE A DETECTED IMPEDANCE

COMPARE THE DETECTED IMPEDANCE
VARIABLE TO A DYNAMICALLY DETERMINED           ∿906
TREATMENT THRESHOLD

TRIGGER AN APPLICATION OF A THERAPEUTIC
MICROCURRENT THROUGH THE TREATMENT
ELECTRODE AND THE PRESENT LOCATION ON
THE USER'S FACE IF THE DETECTED
IMPEDANCE VARIABLE SATISFIES THE
TREATMENT THRESHOLD AND NOT                     ∿908
TRIGGERING THE APPLICATION OF THE
THERAPEUTIC MICROCURRENT IF THE
DETECTED IMPEDANCE VARIABLE DOES NOT
SATISFY THE TREATMENT THRESHOLD

UPDATE THE TREATMENT THRESHOLD USING           ∿910
THE DETECTED IMPEDANCE VARIABLE

MICROCURRENT MIGRAINE TREATMENT DEVICE WITH AN ADAPTIVE TRIGGER

CROSS REFERENCE TO RELATED APPLICATIONS

The present application is a Continuation application which claims priority benefit under 35 U.S.C. § 120 of International Patent Application No. PCT/US2022/029907, entitled "MICROCURRENT MIGRAINE TREATMENT DEVICE WITH AN ADAPTIVE TRIGGER," filed May 18, 2022; which claims priority benefit from U.S. Provisional Patent Application No. 63/189,948, entitled "ADAPTIVE TRIGGER FOR A MICROCURRENT MIGRAINE ALLE-VIATION DEVICE," filed May 18, 2021, each of which, to the extent not inconsistent with the disclosure herein, is incorporated by reference.

SUMMARY

According to an embodiment, a method includes measuring, during a detection mode of a microcurrent migraine treatment device, an electrical impedance between a treatment electrode of the microcurrent migraine treatment device and a return electrode of the microcurrent migraine treatment device as the treatment electrode moves across the skin of a user and the return electrode is in contact with a hand of the user. The method includes establishing, during the detection mode, a trigger condition based on the impedance. The method includes triggering a treatment mode of the microcurrent migraine treatment device when the trigger condition is met, the treatment mode including outputting a signal to the user that the microcurrent migraine treatment device has entered a treatment mode while a therapeutic microcurrent is applied between the treatment electrode and the return electrode through at least a portion of a trigeminal nerve, occipital nerve, auricular nerve, or cervical nerve of the user.

According to an embodiment, a handheld microcurrent migraine treatment device includes a housing configured to be held in a hand of a user, a treatment electrode coupled to the housing, and a return electrode positioned on the housing such that when the user holds the housing, the hand of the user is in contact with the return electrode. The handheld microcurrent migraine treatment device includes a current output circuit configured to pass a treatment microcurrent between the treatment electrode and the return electrode during a detection mode and a treatment mode. The handheld microcurrent migraine treatment device includes an adaptive trigger circuit positioned within the housing and configured to detect an impedance between the return electrode and the treatment electrode as the treatment electrode moves along the skin surface of the user, superjacent a portion of the trigeminal nerve, occipital nerve, auricular nerve, or cervical nerve and to output a signal to the user indicating the device has entered a treatment mode responsive to a detected impedance.

According to an embodiment, a method for applying a therapeutic microcurrent includes using a handheld device, measuring an electrical impedance between a treatment electrode of the handheld device in contact with a person's skin and a return electrode at a surface of the handheld device in contact with the person's hand to produce a detected impedance, converting the detected impedance to a detected impedance, and comparing the detected impedance to a dynamically determined treatment threshold. An application of the therapeutic microcurrent through the treatment electrode and the present location on the person's skin is triggered if the detected impedance satisfies the treatment threshold. The therapeutic microcurrent is not triggered if the detected impedance does not satisfy the treatment threshold. The treatment threshold is updated using the detected impedance.

According to an embodiment, a handheld microcurrent migraine treatment device includes a current output circuit for applying a microcurrent to a triggered location on a human user and an adaptive trigger circuit configured to detect impedance values at locations on a person's skin, dynamically establish a triggering threshold, and trigger the current output circuit for applying the microcurrent when the dynamically established triggering threshold is met.

According to an embodiment, a method includes measuring an electrical impedance between a treatment electrode of a microcurrent migraine treatment device and a return electrode of the microcurrent migraine treatment device contacting the skin of a user as the treatment electrode moves across the skin of the user superjacent the trigeminal nerve, occipital nerve, auricular nerve, or cervical nerve and the return electrode is in contact with a hand of the user. The method includes generating an impedance based on the electrical impedance, comparing the impedance to a treatment threshold, and passing a therapeutic microcurrent between the treatment electrode and the return electrode through the skin of the user responsive to the detected impedance satisfying the treatment threshold.

According to an embodiment, a method for providing a microcurrent treatment for treating human migraine symptoms includes a human user grasping a microcurrent migraine treatment device with a hand, the surface of the microcurrent migraine treatment device supporting a return electrode, such that grasping the microcurrent migraine treatment device makes an electrical coupling between the hand and the return electrode. The microcurrent migraine treatment device is positioned by the user with a treatment electrode in contact with a first skin surface location, the first skin surface location lying superjacent to a trigeminal nerve, superjacent to an auricular nerve, superjacent to an occipital nerve, or superjacent to a cervical nerve. The treatment electrode is insulated from the return electrode such that a current path is formed through the user's body.

BRIEF DESCRIPTION OF THE DRAWINGS

FIG. 8 is a flow chart illustrating an example process of operating a handheld microcurrent migraine treatment device, according to an embodiment.

FIG. 9 is a flow chart illustrating an example process of operating a microcurrent migraine treatment device, according to an embodiment.

DETAILED DESCRIPTION

Figure 1:
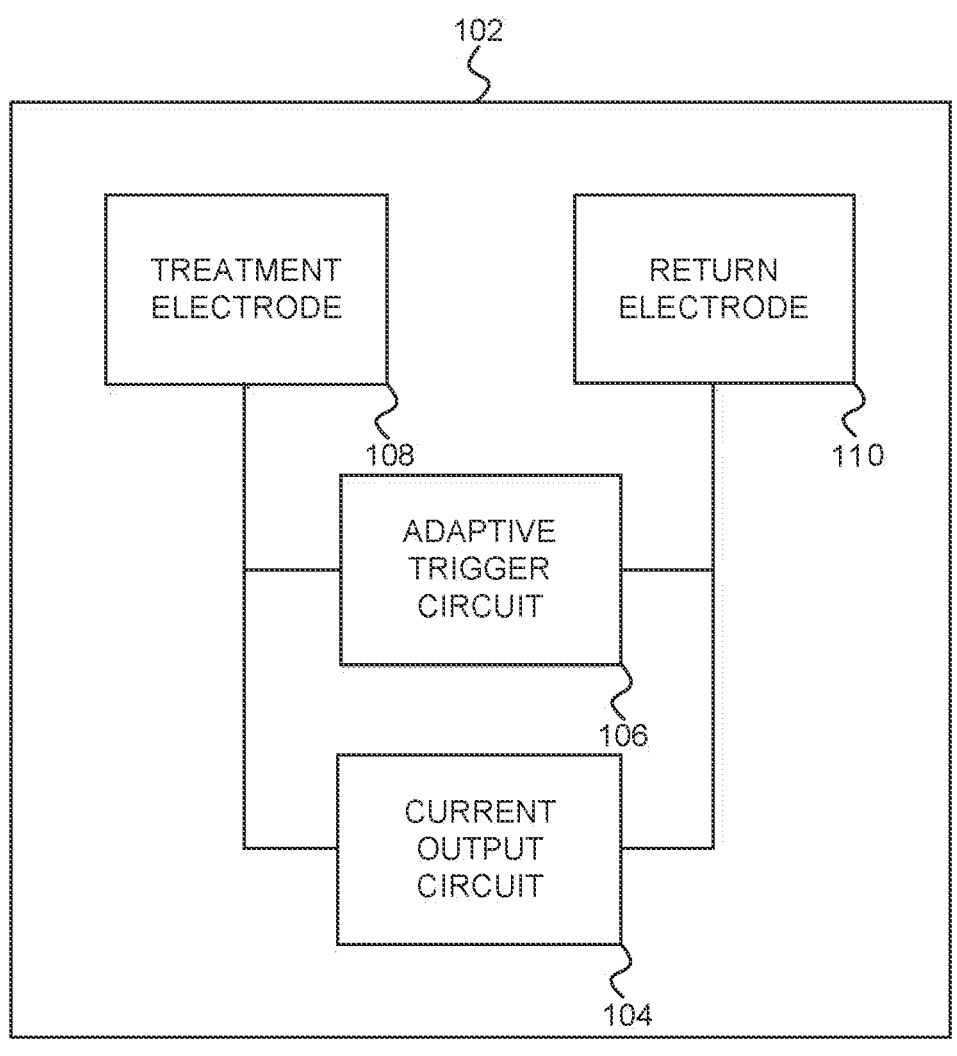
FIG. 1 is a block diagram of a handheld microcurrent migraine treatment device, according to an embodiment.

In the following detailed description, reference is made to the accompanying drawings, which form a part hereof. In the drawings, similar symbols typically identify similar components, unless context dictates otherwise. Other embodiments may be used and/or other changes may be made without departing from the spirit or scope of the disclosure.

FIG. 1 is a block diagram of a handheld microcurrent migraine treatment device 102, according to an embodiment.

According to an embodiment, the handheld microcurrent migraine treatment device 102 is configured to provide migraine relief treatment to a user by providing electrical migraine treatment stimulation to treatment locations superjacent to related nerves, including the trigeminal nerves, occipital nerves, auricular nerves, and cervical nerves of the user. One skilled in the art will realize that nerve morphology and treatment effectiveness may vary from person to person. Accordingly, references to the trigeminal, occipital, auricular, and/or cervical nerves will be understood to refer the nerves in combination or individually, or to one or more of the nerves to the exclusion of the other(s), depending upon context.

In a detection mode, the handheld microcurrent migraine treatment device 102 detects a treatment location by outputting a detection signal to a treatment electrode 108 of the handheld microcurrent migraine treatment device 102 as the user glides the treatment electrode 108 of the handheld microcurrent migraine treatment device 102 over the skin within a treatment area of the user. Electrical current is returned through the body of the user via a return electrode 110. An adaptive trigger circuit 106 receives a sequence of detection signals and derives a dynamic threshold for triggering a treatment mode.

The handheld microcurrent migraine treatment device 102 identifies a treatment location, within the treatment area, based on the detection signal in comparison to the dynamic threshold. When the handheld microcurrent migraine treatment device 102 has identified a treatment location, the handheld microcurrent migraine treatment device 102 enters into a treatment mode. In the treatment mode, the handheld microcurrent migraine treatment device 102 outputs therapeutic current from a current output circuit 104 through the treatment electrode 108. The therapeutic current is selected to provide migraine relief treatment stimulation to the treatment location, thereby providing migraine relief to the user. The user may operate the handheld microcurrent migraine treatment device 102 to identify and provide treatment to multiple treatment locations.

Figure 2A:
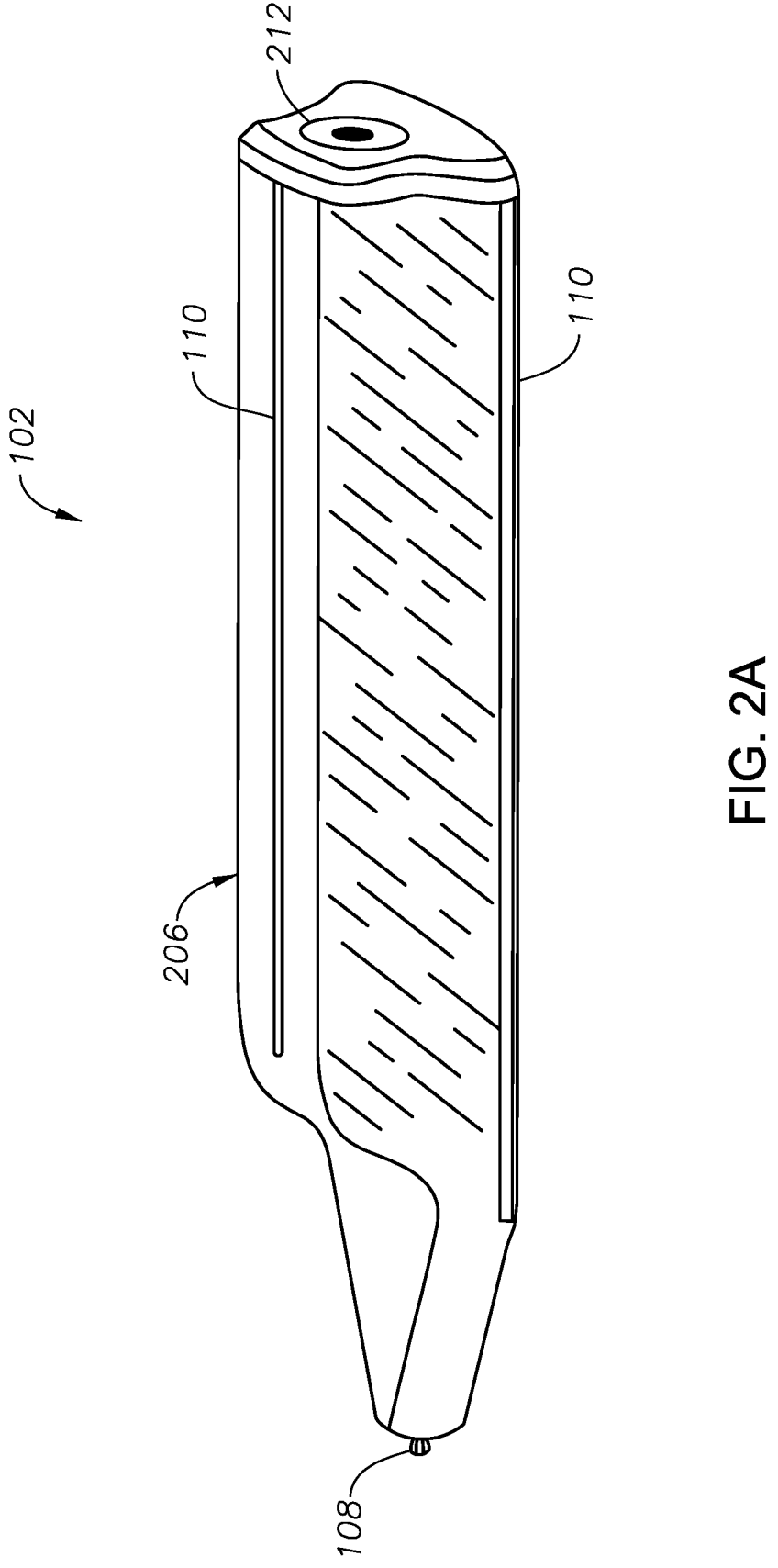
FIG. 2A is a perspective view of a handheld microcurrent migraine treatment device, according to an embodiment.

FIG. 2A is a perspective view of a handheld microcurrent migraine treatment device 102, according to an embodiment. The handheld microcurrent migraine treatment device 102 includes a device body or housing 206, a treatment electrode 108, a return electrode 110, and a charging port 212, according to an embodiment.

According to an embodiment, the device body 206 is a rigid case or housing. The device body 206 has a shape that enables a user of the handheld microcurrent migraine treatment device 102 to securely grip and comfortably hold the handheld microcurrent migraine treatment device 102 during operation of the handheld microcurrent migraine treatment device 102. The device body 206 may be made from a material that is not electrically conductive. The device body 206 may be made from a material that has low thermal conductivity. The device body 206 is configured to protect sensitive electronic circuitry positioned within the device body 206, as is described in more detail with relation to FIG. 3.

According to an embodiment, the treatment electrode 108 is an electrical conductor placed at a tip of the device body 206. The treatment electrode 108 may include a rounded shape at a point of contact with the skin of the user such that the treatment electrode 108 may be placed against the skin of the user comfortably without piercing or scratching the skin. Furthermore, the shape and material of the treatment electrode 108 may be selected to enable the user to comfortably glide the treatment electrode 108 along the skin of the user superjacent to the trigeminal nerve, occipital nerve, auricular nerve, and/or cervical nerve of the user.

According to an embodiment, the return electrode 110 includes an electrically conductive material positioned at various locations on or in the device body 206. The return electrode 110 may be positioned on the device body 206 at positions selected so that when the user holds the handheld microcurrent migraine treatment device 102 in the user's hand, the user's hand is in contact with the return electrode 110 on one or more locations on the device body 206. According to an embodiment, the return electrode 110 may include a conductive polycarbonate or other conductive polymer. In another embodiment, the return electrode 110 may include a conductive metal such as stainless steel, copper, nickel plated copper, chromium plated copper, gold, silver, aluminum, or plated aluminum, for example.

According to an embodiment, the charging port 212 is positioned at the rear of the device body 206 of the handheld microcurrent migraine treatment device 102. The charging port 212 is configured to receive a charging cable.

Figure 2B:
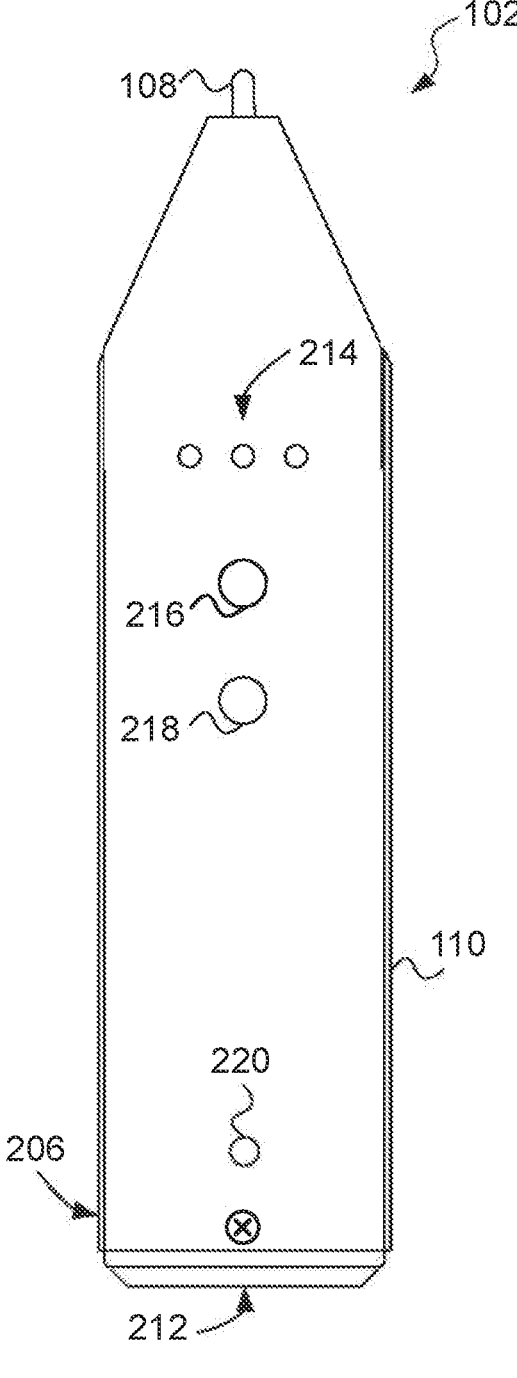
FIG. 2B is a top view of the handheld microcurrent migraine treatment device of FIG. 2A, according to an embodiment.

FIG. 2B is a top view of a handheld microcurrent migraine treatment device 102, according to an embodiment. The top view of the handheld microcurrent migraine treatment device 102 illustrates the device body 206, the treatment electrode 108, the return electrode 110, indicators 214, a sensitivity setting button 216, a power button 218, and a low battery indicator 220.

According to an embodiment, the indicators 214 may provide an indication of the sensitivity level of the handheld microcurrent migraine treatment device 102. According to one embodiment, the sensitivity level corresponds to a sensitivity setting for detecting treatment locations M superjacent the trigeminal nerves, occipital nerves, auricular nerves, and/or cervical nerves of the user. For example, the indicators 214 may provide an indication of a relative level of a dynamically established condition for triggering. The indicators 214 may include multiple LED indicators. The handheld microcurrent migraine treatment device 102 may illuminate one or more of the sensitivity level indicator LEDs 214, according to a sensitivity level of the handheld microcurrent migraine treatment device 102.

According to an embodiment, the sensitivity setting button 216 is configured to enable the user to adjust the sensitivity of the handheld microcurrent device 102 to changes in sensed impedance or to depression of the treatment electrode during a detection mode. In another embodiment, the sensitivity setting button 216 is configured to enable the user to adjust the output current to compensate for the sensitivity of the user to electrical discharge and/or according to user preference.

A greater number of illuminated indicator LEDs 214 may correspond to a higher sensitivity level. A lesser number of illuminated indicator LEDs 214 may correspond to a lower sensitivity level. Alternatively, other schemes for illuminating LEDs to indicate a sensitivity level of the handheld microcurrent migraine treatment device 102 may be utilized. Additionally, the indicators 214 may include indicators other than LEDs. For example, the indicators 214 may include various types of lights, a display panel, or other types of indicators capable of providing an indication of the sensitivity level of the handheld microcurrent migraine treatment device 102. According to an embodiment, the indicators 214 may also signal that a treatment location has been identified, that treatment stimulation is currently being provided, that another treatment location should be identified, or other parameters of operation of the handheld microcurrent migraine treatment device 102.

According to an embodiment, the sensitivity setting button 216 is configured to enable the user to manually adjust the sensitivity (such as to adjust condition for triggering or to adjust a nominal current output) of the handheld microcurrent migraine treatment device 102. The user may manipulate the sensitivity setting button 216 in order to increase or decrease the sensitivity of the handheld microcurrent migraine treatment device 102. For example, the user may press the sensitivity setting button 216 to adjust the sensitivity of the handheld microcurrent migraine treatment device 102. Additionally, or alternatively, the user may toggle or slide the sensitivity setting button 216 in order to adjust the sensitivity of the handheld microcurrent migraine treatment device 102.

Additionally, or alternatively, the sensitivity setting button 216 may include multiple buttons for adjusting the sensitivity of the handheld microcurrent migraine treatment device 102. A first button may be used to decrease the sensitivity. A second button may be used to increase the sensitivity. Additionally, or alternatively, the handheld microcurrent migraine treatment device 102 may include a touchscreen that enables the user to adjust the sensitivity of the handheld microcurrent migraine treatment device 102.

According to an embodiment, the power button 218 is configured to enable the user to turn the handheld microcurrent migraine treatment device 102 on or off. For example, if the handheld microcurrent migraine treatment device 102 is currently off, then the user may turn the handheld microcurrent migraine treatment device 102 on by pressing, toggling, sliding, or otherwise manipulating, the power button 218. If the handheld microcurrent migraine treatment device 102 is currently on, then the user may turn the handheld microcurrent migraine treatment device 102 off by pressing, toggling, sliding, or otherwise manipulating the power button 218. Alternatively, the sensitivity setting button 216 and the power button 218 may be implemented in a single button or switch that may adjust the sensitivity or turn the handheld microcurrent migraine treatment device 102 on or off based on a length of a button press, a number of button presses, or other types of manipulations of the single button.

According to an embodiment, the low battery indicator 220 may provide an indication of a state of charge of the battery of the handheld microcurrent migraine treatment device 102. The low battery indicator 220 may include one or more LEDs. When the battery of the handheld microcurrent migraine treatment device 102 is low, one or more LEDs of the low battery indicator 220 may become illuminated. If the low battery indicator 220 includes a single LED, then the single LED may become illuminated when the battery is nearing depletion. Conversely, the single LED may not be illuminated when the battery is not nearing depletion. Alternatively, when the battery is nearing depletion, a first LED of a first color may be illuminated to indicate that the battery is nearing depletion. If the battery is not nearing depletion, then a second LED of a second color may be illuminated indicating that the battery is not nearing depletion.

According to an embodiment, portions of the return electrode 110 are positioned on the sides of the device body 206 of the handheld microcurrent migraine treatment device 102. When the user grips the handheld microcurrent migraine treatment device 102 such that a thumb of the user is in a position to manipulate the sensitivity setting button 216 and the power button 218, the palm and/or fingers of the hand of the user will be in contact with the portion of the return electrode 110 positioned on the sides of the device body 206 of the handheld microcurrent migraine treatment device 102.

Figure 2C:
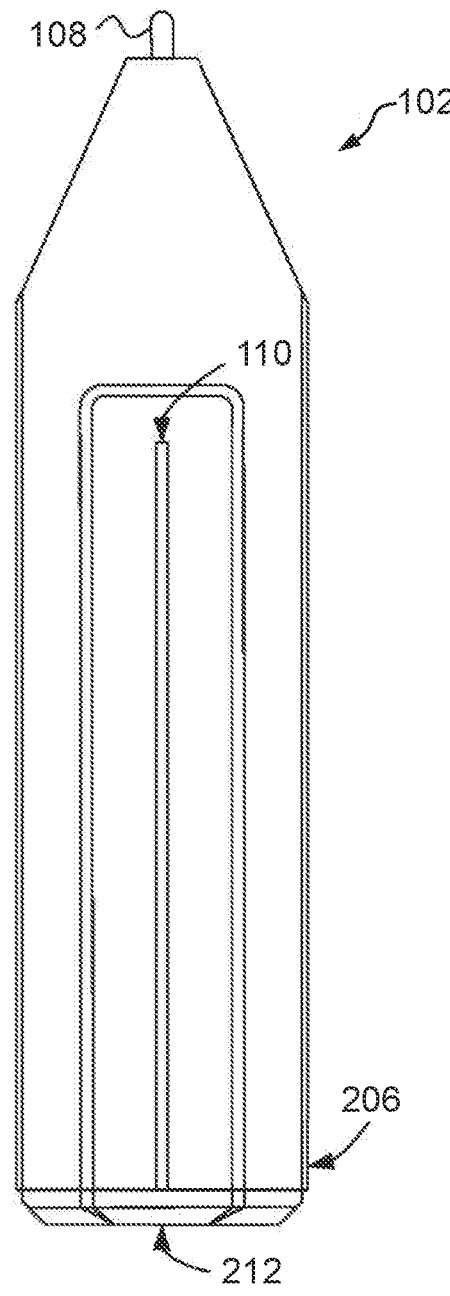
FIG. 2C is a bottom view of the handheld microcurrent migraine treatment device of FIG. 2A, according to an embodiment.

FIG. 2C is a bottom view of the handheld microcurrent migraine treatment device 102 of FIG. 2B, according to an embodiment. The bottom view of the handheld microcurrent migraine treatment device 102 illustrates a portion of the return electrode 110 positioned on the bottom portion of the device body 206 of the handheld microcurrent migraine treatment device 102. The positioning of a portion of the return electrode 110 on the bottom of the device body 206 of the handheld microcurrent migraine treatment device 102 further ensures that when the user holds the handheld microcurrent migraine treatment device 102 in the user's hand, the user's hand will be in contact with the return electrode 110. The treatment electrode 108 and indications of the charging port 212 are also visible in FIGS. 2A and 2C.

Figure 3:
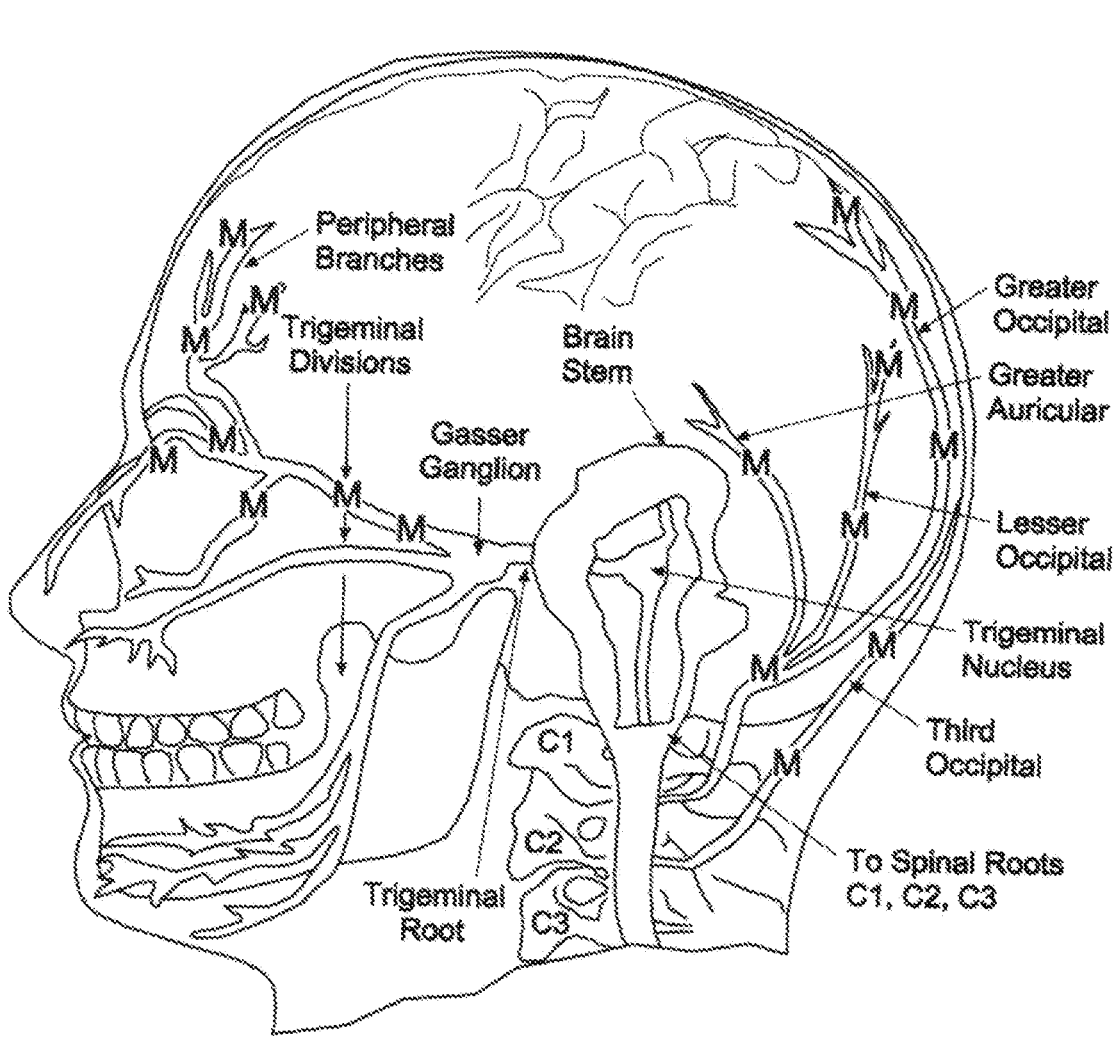
FIG. 3 is an illustration highlighting a plurality of microcurrent migraine treatment areas including treatment locations superjacent the trigeminal nerve, occipital nerve, auricular nerve, and cervical nerve of a user, according to an embodiment.

FIG. 3 is an illustration of a profile of a user of the handheld microcurrent migraine treatment device 102 (e.g., see FIGS. 1 and 2A-2C) highlighting treatment areas and treatment locations M within the treatment areas. According to an embodiment, the treatment locations M correspond to areas superjacent the trigeminal nerves, occipital nerves, and optionally, the auricular nerves and cervical nerves. The treatment locations M are characterized by reduced electrical impedance over the nerves compared to locations between the nerves.

According to an embodiment, the user uses the handheld microcurrent migraine treatment device 102 by holding the device body in one hand such that the user's hand is in contact with portions of the return electrode 110. The user then places the treatment electrode 108 on the skin superjacent an area corresponding to a trigeminal nerve, occipital nerve, auricular nerve, or cervical nerve and glides the treatment electrode 108 over the skin during a detection mode of the handheld microcurrent migraine treatment device 102. In the detection mode, the handheld microcurrent migraine treatment device 102 detects variations in electrical impedance as the user glides the treatment electrode 108 over the skin.

Figure 4:
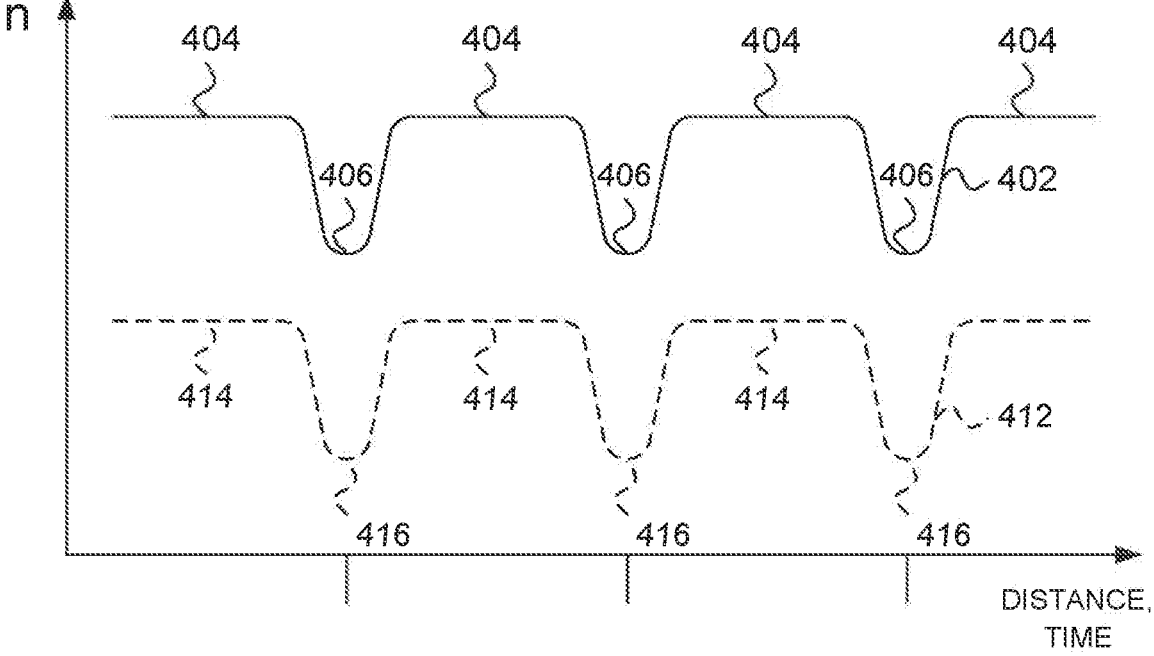
FIG. 4 is a diagram showing impedance variations that may be detected as a treatment electrode is glided over a path across the skin that intersects treatment locations shown in FIG. 3, according to an embodiment.

FIG. 4 is a diagram showing impedance variations that may be detected as the treatment electrode 108 is glided over a path across the skin that intersects several treatment locations M shown in FIG. 3, according to an embodiment. An impedance curve 402 shows ohms (Ω) corresponding to a sequence of locations across the skin of a user. Low impedance regions 406 correspond to treatment locations over nerves shown in FIG. 3. Higher impedance regions 404 separate the low impedance areas 406, the low impedance areas 406 corresponding to the desired treatment locations. A second curve 412 represents an impedance curve measured at a different time. In the second curve 412, higher impedance regions 414 separate low impedance regions 416 corresponding to the desired treatment locations M superjacent to nerves. The second curve 412 may correspond to a second user, for example. Alternatively, the second curve 412 may represent measured impedance across a corresponding skin path at a different time. Relative humidity, hydration, skin oil, and various physiological variations may cause an impedance curve 402 to shift to a second curve 412 at a different time or on a different day. Accordingly, there is a need to accommodate the change in impedance to avoid triggering between nerves and/or to not trigger at all in another instance.

According to an embodiment, the use of a dynamic threshold causes a trigger state to respond to variations in detected impedance, such as are illustrated by FIG. 4, such that a triggering circuit automatically compensates for differences between differences in impedance measured along treatment electrode gliding paths 402 vs. 412. Approaches described herein allow for dynamically determining a triggering condition using an adaptive trigger circuit 106 (FIG. 1).

According to an embodiment, electrical impedance between the treatment electrode 108 of the handheld microcurrent migraine treatment device 102 in contact with a sequence of candidate treatment locations on a person's skin and a current return electrode 110 is detected to produce a sequence of detected impedance values. The detected impedance may optionally be a detected digital impedance value. The detected impedance is compared to a dynamically determined treatment threshold. If the detected impedance satisfies the treatment threshold, the handheld microcurrent migraine treatment device 102 enters a treatment mode. If the detected impedance does not satisfy the treatment threshold, the handheld microcurrent migraine treatment device 102 continues in the detection mode. The treatment threshold is updated using the most recently detected impedance. In some embodiments, the treatment threshold is only updated if the detected impedance does not satisfy the treatment threshold. In other embodiments, the treatment threshold is updated whether or not the most recently detected impedance satisfies the treatment threshold.

The inventors contemplate several approaches to performing adaptive triggering.

According to an embodiment, the dynamically determined impedance threshold comprises a dynamically determined impedance value and satisfaction of the impedance threshold occurs when the detected impedance has a value equal to or less than the dynamically determined impedance value.

According to an embodiment, an averaging circuit creates the dynamic threshold as 80% of an average digital impedance value for the higher impedance regions 404. If the detected impedance has a value less than 80% of the average digital impedance value for three successive measurements, then the dynamic threshold is satisfied and a therapeutic current is applied. If the detected impedance has a value greater than 80% of the average digital impedance value, then the dynamic threshold is not satisfied and the most recent detected impedance is averaged into the average for the higher impedance regions 404. Other thresholds may be substituted for 80% of the high impedance average and different numbers of successive measurements may be applied. For example, in one embodiment, the noise filter (the number of successive measurements) may be decreased if the detected impedance has a lower value. In another embodiment, a higher threshold of 90% of the high impedance average may be used.

According to an embodiment, the dynamically determined impedance threshold is generated as a selected percentage of an average impedance of a plurality of previously detected impedance values.

In another embodiment, the detected impedance values are distributed into a bimodal distribution. High impedance measurements are averaged into a non-treatment area average. Low impedance measurements are averaged into a treatment location M average. A dynamic threshold equal to halfway between the non-treatment area average and the treatment location M average may be set, wherein the therapeutic microcurrent is applied if some number of most recent detected impedance values fall below the treatment threshold. Other thresholds may be substituted for halfway between the non-treatment area average and the treatment location average. For example, treatment may be applied closer to the center of the treatment locations M by selecting an impedance threshold lower than halfway between the non-treatment area and the treatment location M averages. Optionally, a user-controlled sensitivity setting may select from amongst a range of thresholds between the two ranges. According to an embodiment, one approach for changing triggering impedance is to provide a sensitivity setting button 216 (FIG. 2B) for manually selecting a "sensitivity" for the triggering circuit. In another embodiment, a "sensitivity" selection leaves the triggering circuit 106 operating the same but results in a difference in current output by the microcurrent migraine treatment current output circuit 104.

According to an embodiment, a slope between a number of adjacent measurement points is determined, with the treatment threshold corresponding to an average slope in detected impedance between a number of most recent measurements. Higher slopes correspond to larger excursions in impedance, which correspond to lower values of impedance at the low impedance regions 406. In an embodiment, slope vs. distance may be estimated as a difference in successive measurements. Three to five successive slopes that exceed an average slope between successive measurements in a higher impedance region 404 by at least 20% may constitute a treatment threshold.

According to an embodiment, as impedance decreases from a higher impedance region 404 entering a low impedance region 406, curvature (second derivative) successively increases as the impedance decreases, then curvature decreases as the curve passes through an inflection point, then curvature increases again as impedance approaches a minimum. An inflection point may operate as an estimate of an edge between a non-treatment area (higher impedance region 404) and a treatment location M (low impedance region 406). In practice, second derivative in a digital processor may be approximated as a difference between successive differences in digital impedance value. Since both the upper edges and the bottoms of the treatment areas (low impedance treatment locations 406) have high curvature, a region of zero curvature between a region of high negative curvature and a region of high positive curvature, over an appropriate number of samples, represents an edge of a treatment location M (low impedance region 406).

According to an embodiment, two or more detected impedances may be compared to a corresponding two or more thresholds to determine a global threshold for the detection of a treatment location M (low impedance region 406). For example, crossing an edge between a non-treatment area (higher impedance region 404) and a treatment location M (low impedance region 406) may be estimated by requiring a relatively high slope (first derivative) AND requiring a change in sign of a curvature (second derivative).

According to an embodiment, temporal proximity to a most recent treatment may be used in combination with one or more thresholds to determine a triggering state. As may be appreciated from inspection of FIG. 3, the treatment locations M are dispersed across the skin. In practice, impedance measurements are taken at frequent intervals compared to the ability of a person to glide the treatment electrode 108 across his or her skin. Accordingly, if a new threshold is satisfied too quickly, for example less than 100 milliseconds or 250 milliseconds, after the most recent completed treatment, it may be inferred that the new threshold satisfaction does not represent encountering a new treatment location M, and triggering may optionally be suppressed.

According to an embodiment, it is desirable, for effective treatment, to apply a therapeutic microcurrent to a point sufficiently close to a treatment location M for a majority of the current to pass along the nerve fiber. This situation may be satisfied if the treatment electrode 108 is within 2 to 5 millimeters of the center of a nerve. Accordingly, the determination of a treatment threshold being satisfied may be considered generally close enough if the treatment electrode 108 is within such a conduction distance of the treatment location, according to one embodiment.

According to an embodiment, in the treatment mode, the handheld microcurrent migraine treatment device 102 provides treatment stimulation to the treatment location M, corresponding to the nerve that is located during the detection mode. The handheld microcurrent migraine treatment device 102 may provide treatment stimulation to the treatment location M by providing electrical stimulation to the treatment location M. The electrical stimulation may affect the treatment location M in the treatment area in such a way that the user experiences relief from troubling migraine symptoms such as pain or other unpleasant symptoms. The electrical microcurrent stimulation may affect migraine symptoms in two ways. First, electrical stimulation of the nerve fibers may act directly to reduce symptoms. Secondly, the electrical stimulation may provide stimulate tissue (such as muscles) in a way that reduces conditions coincident with migraine symptoms.

According to an embodiment, the handheld microcurrent migraine treatment device 102 is a transcutaneous electrical nerve stimulation (TENS) device. The handheld microcurrent migraine treatment device 102 applies electrical treatment stimulation in the form of a microcurrent having selected characteristics. The microcurrent may have an average magnitude that is orders of magnitude lower than common TENS devices. According to an embodiment, the microcurrent does not have a DC component, and is characterized by current spikes of alternating polarity. According to an embodiment, the microcurrent waveform (see FIG. 7) may be characterized as a biphasic AC-coupled waveform based on a square wave, the AC-coupling causing flat tops and bottoms of the square wave to be suppressed. According to an embodiment, the treatment stimulation is provided at each treatment location M for a period of time between five and sixteen seconds treatment mode duration. According to an embodiment, a treatment mode lasts about eight seconds.

According to an embodiment, the treatment electrode 108 is the active electrode of a monopolar design. The housing/device body 206 of the handheld microcurrent migraine treatment device 102 may serve as the return electrode 110 when return electrodes 110 are integrated into the device body 206. A user's hand holding the handheld microcurrent migraine treatment device 102 completes the electrical path from the conductive treatment electrode 108 to the return electrode(s) 110 in that microcurrents may travel from the conductive treatment electrode 108, through tissues underlying the treatment electrode 108, through the body of the user and through the hand of the user that is contacting the return electrode(s) 110, in an embodiment. The microcurrent may be referred to as "stimulation current" in this disclosure.

According to an embodiment, in the detection mode, the user presses the conductive treatment electrode 108 to the skin and the handheld microcurrent migraine treatment device 102 closes a circuit that is maintained at a constant peak current. The handheld microcurrent migraine treatment device 102 may use the current to calculate the impedance in the path between the tissue at the treatment electrode 108 and the hand in contact with the handheld microcurrent migraine treatment device 102. The handheld microcurrent migraine treatment device 102 remains in the detection mode until the detection current indicates that a treatment threshold has been satisfied. The position of the treatment electrode 108 when the impedance meets the treatment threshold corresponds to a treatment location M. When the handheld microcurrent migraine treatment device 102 identifies a treatment location M based on a comparison of a detected impedance to a dynamically determined treatment threshold, the handheld microcurrent migraine treatment device 102 may enter the treatment mode and may deliver treatment stimulation to the identified treatment location M.

According to an embodiment, the handheld microcurrent migraine treatment device 102 may indicate to the user that the handheld microcurrent migraine treatment device 102 is in the treatment mode and that the user should hold the treatment electrode 108 at the treatment location M for a selected period of time (e.g., about eight seconds). According to an embodiment, the handheld microcurrent migraine treatment device 102 may indicate the transition between the detection mode and the treatment mode by the indicators 214. The indicators 214 may include one or more LEDs that may provide an illumination scheme that indicates whether the handheld microcurrent migraine treatment device 102 is in the detection mode or the treatment mode. According to an embodiment, the handheld microcurrent migraine treatment device 102 may indicate that the handheld microcurrent migraine treatment device 102 is in the treatment mode via haptic feedback (vibration). According to an embodiment, the handheld microcurrent migraine treatment device 102 may indicate whether the handheld microcurrent migraine treatment device 102 is in the detection mode, the treatment mode, or transitioning between the detection and the treatment modes by a combination of haptic feedback and the LED indicators 214. According to an embodiment, when the handheld microcurrent migraine treatment device 102 enters the treatment mode as indicated by one or more of the LED indicators 214 and haptic feedback, the indicators prompt the user to hold the handheld microcurrent migraine treatment device 102 in place until the treatment period has passed as indicated by cessation of haptic feed-back and the LED indicators 214 (approximately 8 seconds in one example).

According to an embodiment, once the treatment period ends, the handheld microcurrent migraine treatment device 102 resets to detection mode. The user then may continue to glide the handheld microcurrent migraine treatment device 102 along a path across the treatment area until reaching a next treatment location M as identified based on a new comparison of a detected impedance to the dynamically determined treatment threshold. The user may adjust the impedance sensitivity of the handheld microcurrent migraine treatment device 102, in one embodiment. Changes in sensitivity may adjust the impedance threshold at which the handheld microcurrent migraine treatment device 102 will enter treatment mode and do not change the output current, in one embodiment. In another embodiment, changes in the dynamically determined treatment threshold correspond to differences in impedance, and the change in sensitivity may be used to correct for a different impedance in order to maintain approximately constant peak current during treatment. According to another embodiment, changes in sensitivity do not affect the dynamically deter-mined treatment threshold, but rather affect a current output of the microcurrent waveform.

According to an embodiment of a treatment circuit of the handheld microcurrent migraine treatment device 102, the constant peak current stimulation output is an approximately 1 Hz-100 Hz, bi-phasic, no DC component signal with a time-averaged current of approximately 360 microamps over a resistive load of 10K-500K ohms. According to an embodiment, a spring-loaded tip activates the current output circuit and gently ramps the current to provide maximal comfort to the user.

According to an embodiment, a stimulation circuit output is directed to the active treatment electrode 108 (the device tip) and returned to the circuit by way of the return electrode 110 (metallized portions of the enclosure). When the circuit is completed by the user pressing the device tip 108 to the skin, a microcontroller monitors the resulting stimulation current and controls the stimulation voltage (across the treatment electrode 108 and the return electrode 110) to maintain the desired peak current, in one embodiment. The impedance of the circuit is then calculated and monitored by the microcontroller. In the event that the impedance falls below a specified threshold, which is indicative of a treat-ment location M, the microcontroller presents a treatment prompt through a user interface (UI), in one embodiment. According to an embodiment, the user is instructed to maintain the treatment electrode 108 at an identified location until the treatment prompt has timed out. After treatment time out, the user is instructed to move the treatment electrode 108 across the treatment area until the microcur-rent treatment device detects a next treatment location M, in one embodiment.

According to an embodiment, the sensitivity level setting determines the impedance threshold at which the handheld microcurrent migraine treatment device 102 will signal the user to detection of a treatment location M. The treatment sensitivity threshold may be increased to compensate for higher impedance associated with dry skin or the presence of makeup, in one embodiment. Upon detection of a treatment location M, the haptic motor starts to vibrate and the sensitivity level indicator LEDs 214 flash for a pre-pro-grammed period of time, in one embodiment. If the calcu-lated impedance increases above the threshold (treatment electrode 108 removed from the skin or moved to a higher impedance location on the skin), the treatment session may be terminated early and the device returned to the detection mode.

Figure 5:
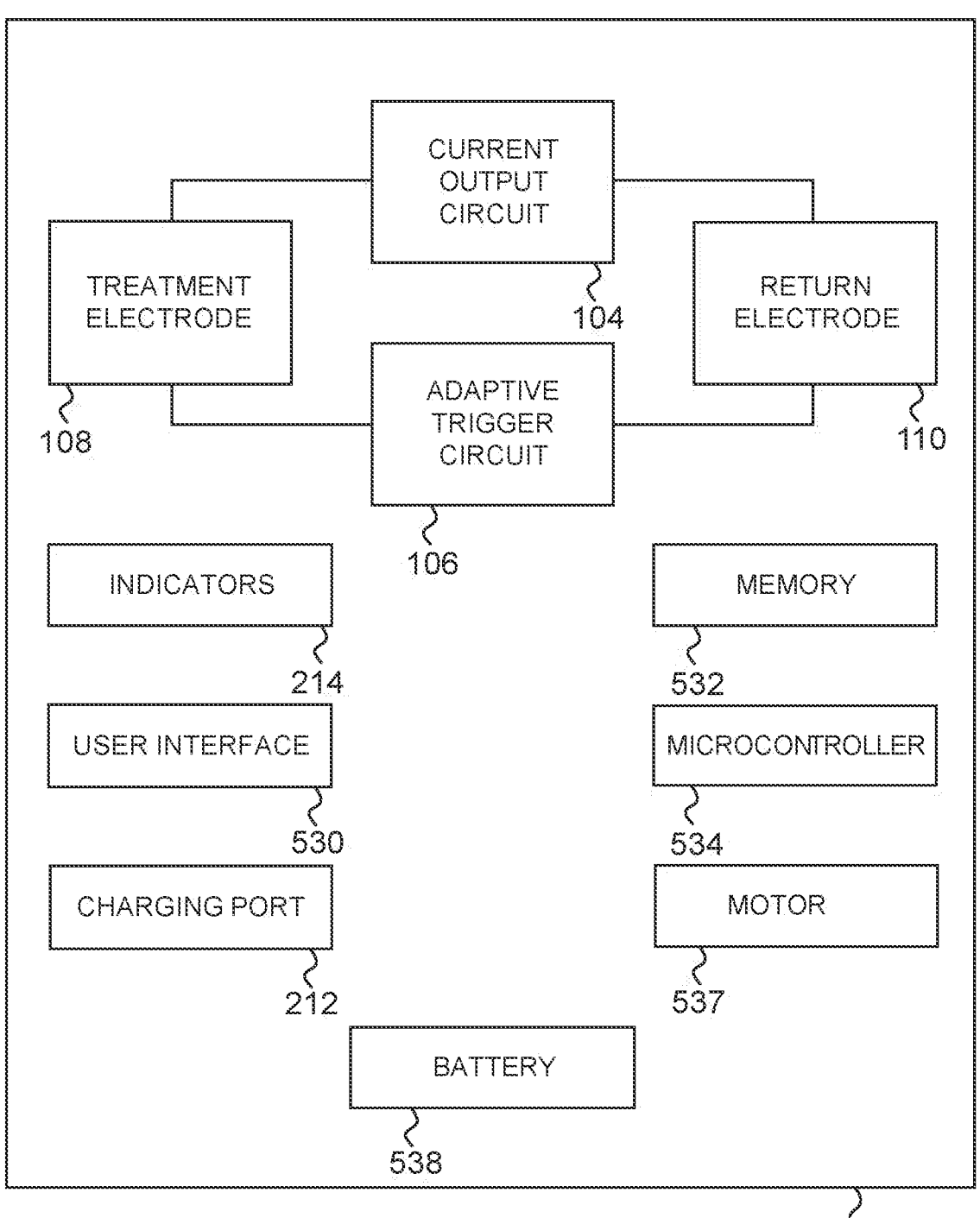
FIG. 5 is a block diagram of a handheld microcurrent migraine treatment device, according to an embodiment.

FIG. 5 is a block diagram of the handheld microcurrent migraine treatment device 102, according to an embodiment. The handheld microcurrent migraine treatment device 102 includes a treatment electrode 108, a return electrode 110, a current output circuit 104, an adaptive trigger circuit 106, the charging port 212, indicators 214, a user interface 530, a memory 532, a microcontroller 534, a motor 537, and a battery 538. The current output circuit 104 is shown as separate from the treatment electrode 108 and the return electrode 110 for purposes of clarity. Similarly, the current output circuit 104 is shown as separate from the adaptive trigger circuit 106 for purposes of clarity. In practice, both circuits 104, 106 may use a common current source, but with a voltage divider or resistance being placed between select-able nodes of the circuit. The handheld microcurrent migraine treatment device 102 utilizes these components to provide effective migraine relief treatments to the user.

According to an embodiment, the treatment electrode 108 and the return electrode 110 cooperate together to provide both detection currents and treatment stimulation. Detection and treatment currents are passed between the treatment electrode 108 and the return electrode 110 through the body of the user. In particular, the treatment electrode 108 is positioned in contact with the user's skin to the migraine areas (e.g., over the trigeminal, occipital, auricular, or cer-vical nerves) of the user. The return electrode 110 is in contact with the user's hand as the user holds the handheld microcurrent migraine treatment device 102. The detection and treatment current passes between the treatment electrode 108 and the return electrode 110 via the hand, body, and treatment location M of the user.

According to an embodiment, the indicators 214 provide indications to the user as to the present mode of operation of the handheld microcurrent migraine treatment device 102. The indicators 214 may include one or more LEDs that may be illuminated in selected ways to indicate whether the handheld microcurrent migraine treatment device 102 is powered on, whether the handheld microcurrent migraine treatment device 102 is in a treatment mode, whether the handheld microcurrent migraine treatment device 102 is in a detection mode, whether the handheld microcurrent migraine treatment device 102 awaits user input, or indica-tions of other types of functionality of the handheld micro-current migraine treatment device 102. According to an embodiment, the indicators 214 may include a display capable of outputting text or images to indicate to the user the various functions of the handheld microcurrent migraine treatment device 102.

According to an embodiment, the user interface 530 includes various components that enable the user to control functionality of the handheld microcurrent migraine treat-ment device 102. The user interface 530 may include the on-off power button 218, the sensitivity setting button 216, or other kinds of buttons, switches, touchscreens, or input controls that enable the user to control functionality of the handheld microcurrent migraine treatment device 102. The user may manipulate the user interface 530 in order to control the functionality of the handheld microcurrent migraine treatment device 102.

According to an embodiment, the memory 532 stores data related to the functionality of the handheld microcurrent migraine treatment device 102. The memory 532 may include software instructions by which the various function-alities of the handheld microcurrent migraine treatment device 102 may be implemented. The memory 532 may include reference impedance values and/or threshold impedance values. The reference and threshold impedance values may be utilized in the detection mode of the handheld microcurrent migraine treatment device 102. The memory 532 may include data indicating previously detected treatment locations M. The memory 532 may include other settings such as treatment lengths, treatment stimulation strengths, frequencies of treatments, or other settings including default settings and user selected settings for operation of the handheld microcurrent migraine treatment device 102. The memory 532 may include one or more of EEPROMs, flash memory, ROMs, SRAM, DRAM, or other kinds of computer readable media capable of storing instructions that may be executed by the microcontroller 534.

According to an embodiment, the motor 537 enables the handheld microcurrent migraine treatment device 102 to provide haptic feedback to the user. For example, during a detection mode and a treatment mode in which the handheld microcurrent migraine treatment device 102 provides stimulation treatment to a treatment location M, the motor 537 may cause the handheld microcurrent migraine treatment device 102 to vibrate mildly to indicate to the user that the handheld microcurrent migraine treatment device 102 is in the treatment mode. The motor 537 may cease the vibration to indicate that the handheld microcurrent migraine treatment device 102 is no longer in the treatment mode. The motor 537 may generate vibrations to provide a variety of types of indications to the user of the handheld microcurrent migraine treatment device 102.

According to an embodiment, the battery 538 provides power to the handheld microcurrent migraine treatment device 102. The battery 538 may include a rechargeable battery that enables the user to recharge the battery 538 after the battery 538 has become depleted through use. The battery 538 may be a lithium-ion battery, a NiCad battery, a carbon zinc battery, an alkaline battery, a nickel metal hydride battery, or other types of batteries.

According to an embodiment, the charging port 212 enables the user to recharge the battery 538. For example, the charging port 212 may be configured to receive a charging cable that connects the charging port 212 to a power source. When the charging cable is connected to the charging port 212, the internal battery of the handheld microcurrent migraine treatment device 102 is recharged. Additionally, or alternatively, the charging port 212 may be a power supply port configured to connect to a power cable that provides power to the handheld microcurrent migraine treatment device 102 while the user is using the handheld microcurrent migraine treatment device 102. The charging port 212 may include a micro USB port, a USB 2.0 port, a USB 3.0 port, a USB C port, or other type of port that may be utilized to charge the battery of the handheld microcurrent TMJ symptom treatment device 102, or to otherwise provide power to the handheld microcurrent TMJ symptom treatment device 102. According to an embodiment, the charging port 212 enables charging and data transmission. When a charging cable is plugged into the charging port 212, the battery 538 may be charged and data may be received or transmitted over the charging cable via the charging port 212. According to an embodiment, the handheld microcurrent migraine treatment device 102 may operate while a charging cable is attached to the charging port 212. Thus, if the battery 538 is depleted, the user may attach a charging cable to the charging port 212 and may operate the handheld microcurrent migraine treatment device 102 from power received via the charging port 212. Additionally or alternatively, the handheld microcurrent migraine treatment device 102 may include wireless charging capability. For example, the handheld microcurrent migraine treatment device 102 may include circuitry that enables inductive charging of the battery of the handheld microcurrent migraine treatment device 102 such that when the handheld microcurrent migraine treatment device 102 is positioned on a charging dock, the battery is recharged by inductive charging.

According to an embodiment, the microcontroller 534 controls the functionality of the other components of the handheld microcurrent migraine treatment device 102. The microcontroller 534 is communicatively coupled to the treatment electrode 108, the return electrode 110, the indicators 214, the memory 532, the user interface 530, and the charging port 212.

According to an embodiment, the microcontroller 534 executes the software instructions stored in the memory 532 to implement the various modes of functionalities of the handheld microcurrent migraine treatment device 102. The microcontroller 534 causes the treatment electrode 108 and the return electrode 110 to pass the detection currents in the detection mode, and to pass the treatment microcurrents in the treatment mode. The microcontroller 534 controls the indicators 214 to indicate the various modes of functionalities of the handheld microcurrent migraine treatment device 102. The microcontroller 534 communicates with the user interface 530 to enable the user to select various modes of operation of the handheld microcurrent migraine treatment device 102.

Figure 6:
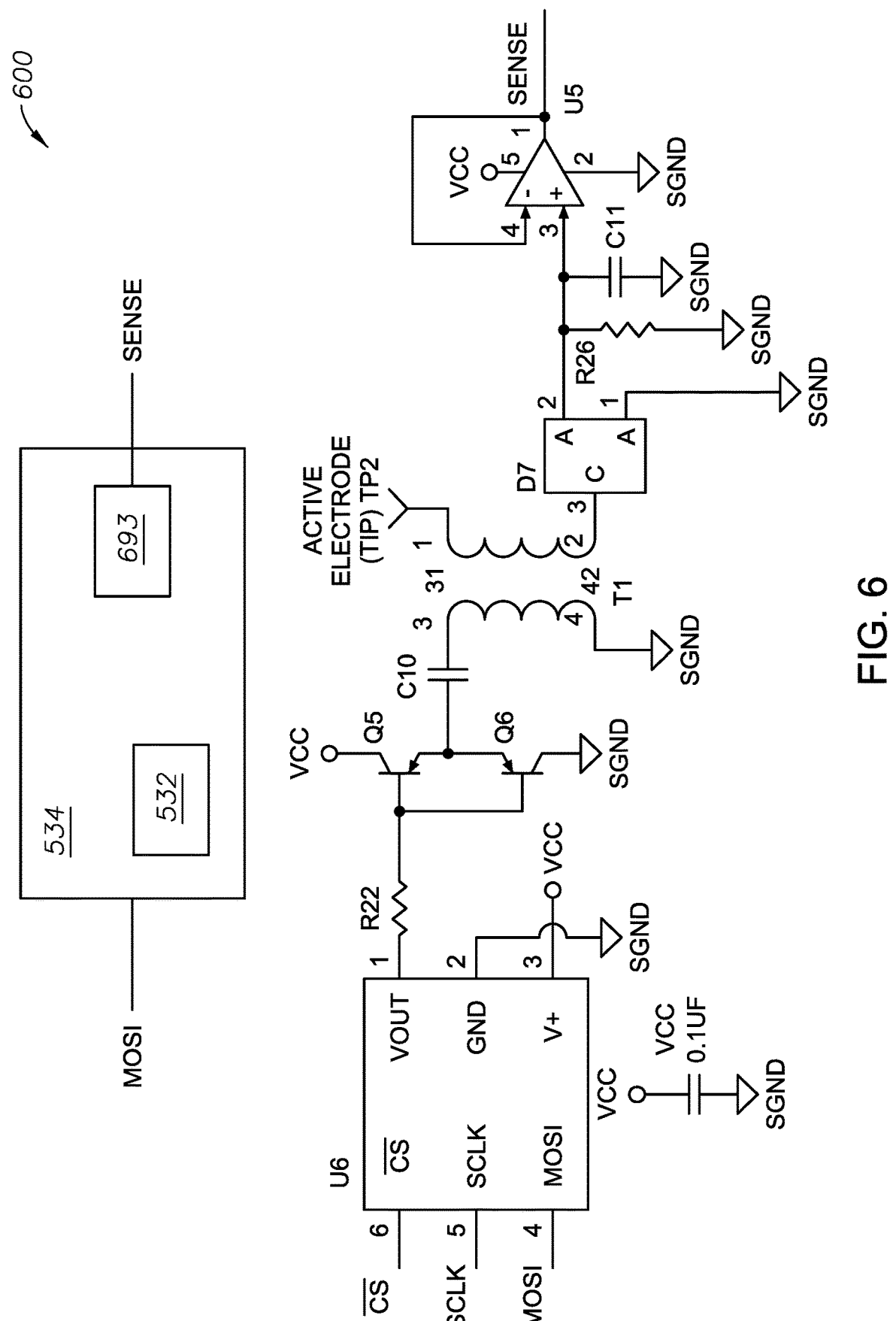
FIG. 6 illustrates an example of microcurrent migraine treatment circuitry for use with a microcurrent migraine treatment device, according to an embodiment.

FIG. 6 illustrates an example microcurrent migraine treatment circuit 600 for use with the handheld microcurrent migraine treatment device 102, according to an embodiment of the disclosure. The microcurrent migraine treatment circuitry 600 is positioned within the housing/device body 206, according to one embodiment. The microcurrent migraine treatment circuit 600 includes a microcontroller 534 including a memory 532 and an analog-to-digital converter (ADC) 693. In the illustrated embodiment of FIG. 5, the microcurrent migraine treatment circuitry 600 also includes a stimulation driver stage and a peak detector.

According to an embodiment, the stimulation driver stage is coupled to apply a stimulation voltage between the treatment electrode (active electrode TP2) and the return electrode 110 (not illustrated in FIG. 5). In the illustrated embodiment, the stimulation driver stage includes a digital-to-analog converter (DAC), an amplifier, a transformer, and a capacitor. According to an embodiment, the DAC (U6) is coupled to generate an analog voltage (pin 1 of U6, VOUT) in response to a digital instruction from the microcontroller 534 received via the MOSI (Master Out Slave In) communication channel of pin 4 of U6.

In the illustrated embodiment, the amplifier includes transistors Q5 and Q6 and is coupled to generate an amplified analog voltage (emitter node of Q5) in response to receiving the analog voltage from the DAC U6.

In the illustrated embodiment, the transformer T1 includes a primary side (nodes 3 and 4) and a secondary side (nodes 1 and 2). The treatment electrode (active electrode TP2) is coupled to node 1 of the secondary side of the transformer T1, in the illustrated embodiment.

In the illustrated embodiment, capacitor C10 is coupled between the amplifier and a primary side of the transformer T1 to block the DC (direct current) portions of the amplified analog signal.

According to an embodiment, the peak detector includes a diode element, a buffer circuit, and a sample and hold circuit. In the illustrated embodiment, the diode element is D7. According to an embodiment, the buffer circuit is coupled to output a peak stimulation current signal. According to an embodiment, the peak detector is coupled to generate a peak stimulation current signal on the node 1 output of op-amp U5 in response to receiving a stimulation signal from the treatment electrode. In the illustrated embodiment, the stimulation signal may travel from the treatment electrode TP2 to node 2 of the transformer T1 via node 1 of the transformer T1.

According to an embodiment, the sample and hold circuit is coupled between the diode element D7 and the buffer circuit and the diode element is coupled between the secondary side of the transformer and the sample and hold circuit. In the illustrated embodiment, the sample and hold circuit includes resistors R26 and capacitor C11.

According to an embodiment, the microcontroller 534 is coupled to receive the peak stimulation current signal (SENSE) from the peak detector and coupled to the stimulation driver stage for adjusting the stimulation voltage in response to the peak stimulation current signal. According to an embodiment, the microcontroller 534 dynamically adjusts the stimulation voltage to keep the peak stimulation current signal at a constant value. According to an embodiment, microcontroller 534 includes ADC 693 coupled to sample the peak stimulation current signal and drive the digital instruction to the DAC (via MOSI communication channel) to keep the peak stimulation current signal at the constant value.

The microcurrent migraine treatment circuit 600 of FIG. 6 provides a means to maintain a nearly constant (and comfortable) peak stimulation current in response to varying resistance or impedance. Turning to a more specific description of an embodiment of microcurrent migraine treatment circuitry 600, a digital-to-analog converter (DAC) U6 receives commands from the microcontroller 534 to generate a square wave with a variable amplitude of 0 to +Vcc volts. The DAC output is current limited by R22 and is used to drive a push-pull output power stage comprised of Q5 and Q6, in the illustrated embodiment. The output of the push-pull stage is AC coupled by C10 and drives the primary side of a step-up transformer T1. C10 blocks the DC component of the square wave and allows through only the rising and falling edges of the square wave. The transformer converts the high current, low voltage edge input to the high voltage, low (microcurrent) stimulation current output, in the illustrated embodiment.

One end of the secondary side of the transformer is connected to the treatment electrode. The other end of the secondary coil is connected to a dual diode array D7. The diode array acts as the stimulation current positive peak detector. R26 and C11 provide a simple sample and hold function of the detected peak. The peak detector output is buffered by op-amp U5. The output of the op-amp is then sampled by the ADC of the microcontroller.

During use, a control loop is formed by the DAC, peak detector, and the microcontroller ADC. The sensed positive peaks of the stimulation current are maintained at a constant level by controlling the DAC output. As the total resistance decreases, the control loop reduces the DAC output which reduces the amplitude of the edges being input to the transformer. The control loop effectively converts the voltage source output of the transformer to a constant current source, in the illustrated embodiment. In this manner, any uncomfortable surges in current are reduced during treatment.

Figure 7:
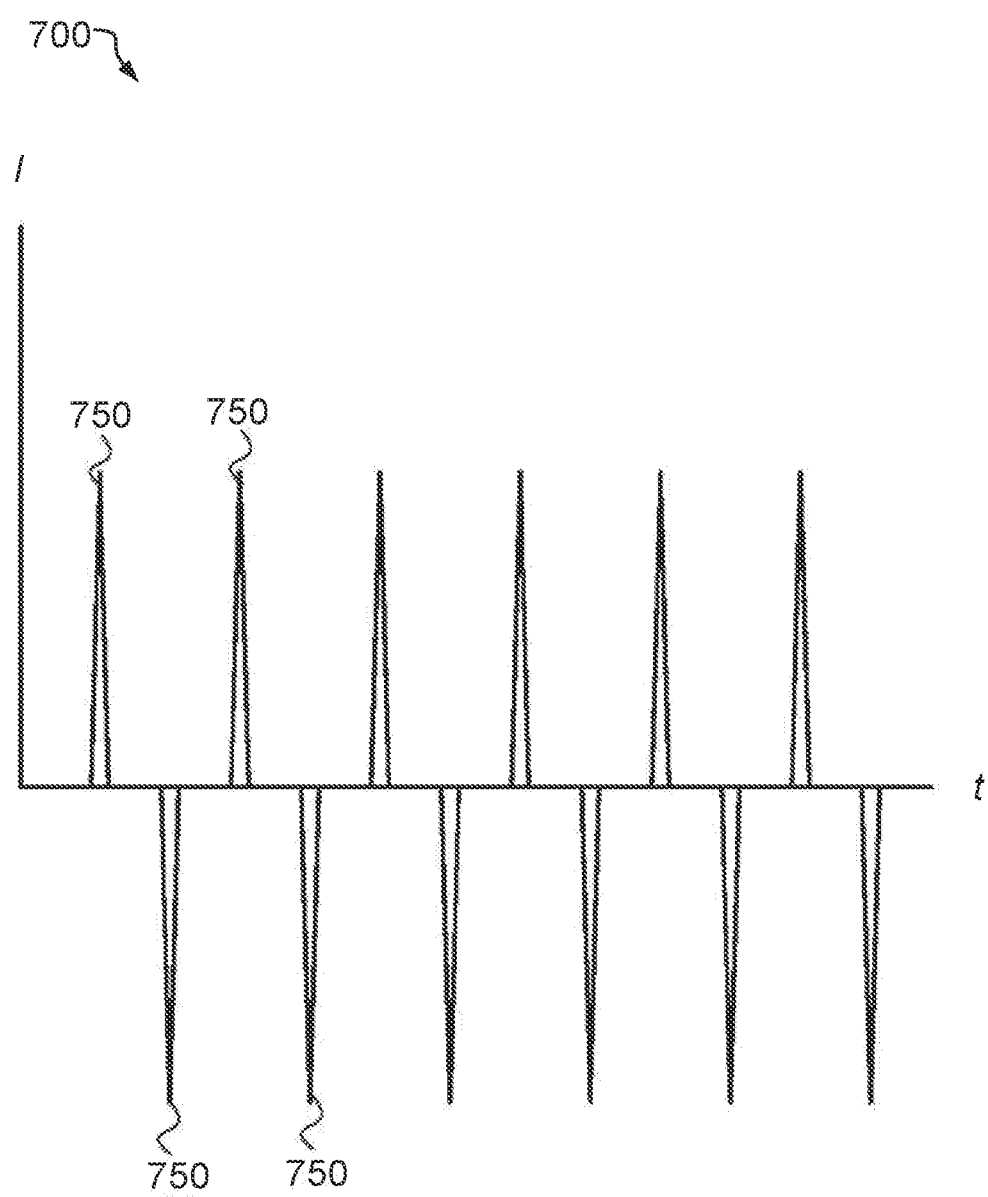
FIG. 7 is a waveform of a treatment current vs time, according to an embodiment.

FIG. 7 is a waveform 700 of a treatment microcurrent (I) vs time (t), according to an embodiment. The treatment microcurrent is applied during a detection mode and a treatment mode of the handheld microcurrent migraine treatment device 102 including after the handheld microcurrent migraine treatment device 102 has identified a treatment location M. The treatment microcurrent provides relief to migraine discomfort.

According to an embodiment, the treatment microcurrent corresponds to a series of sharp current spikes 750 or peaks. According to an embodiment, successive current spikes 750 alternate in polarity such that every other current spike 750 flows in a first polarity, while intervening current spikes 750 flow in a second, opposite, polarity. According to an embodiment, the current spikes 750 correspond to the rising and falling edges of a square wave voltage signal. According to an embodiment, the treatment microcurrent is generated by feeding a square wave voltage signal to a transformer, such as the transformer T1, via a capacitor, such as the capacitor C10. Those of skill in the art will recognize, in light of the present disclosure, that a treatment microcurrent in accordance with FIG. 7 may be generated in various ways. All such other ways for generating the treatment microcurrent fall within the scope of the present disclosure.

According to an embodiment, the treatment microcurrent has no DC offset. The lack of a DC offset may enhance the therapeutic effect of the treatment microcurrent. This is because, in one interpretation, the rapid changes in current magnitude and polarity promote physiological effects that do not occur in the presence of a DC current.

According to an embodiment, the microcurrent migraine treatment circuit 600, including the microcontroller 534 and the memory 532, adjust the stimulation voltage between the treatment electrode 108 and the return electrode 110 to maintain a constant peak microcurrent during the treatment mode. According to an embodiment, maintaining a constant peak microcurrent corresponds to causing the peaks of the treatment microcurrent to have substantially the same magnitudes. According to an embodiment, maintaining a constant treatment microcurrent corresponds to causing the peaks of the treatment microcurrent to have substantially the same absolute values. Thus, the positive current peaks and the negative polarity current peaks have the same absolute value, in one embodiment.

According to an embodiment, the peaks of the migraine treatment microcurrent have a magnitude greater than 15 milliamps. According to an embodiment, the peaks of the treatment microcurrent have a magnitude less than 24 milliamps. According to an embodiment, the migraine treatment microcurrent has a nominal peak current of 18 milliamps.

According to an embodiment, the duty cycle of the biphasic AC-coupled migraine treatment waveform 700 is less than 5%. According to an embodiment, the duty cycle of the migraine treatment waveform is about 2%.

According to an embodiment, the migraine symptom treatment microcurrent waveform has a time-averaged current of less than 300 microamps. According to an embodiment, the migraine symptom microcurrent has a time-averaged current of greater than 60 microamps. According to an embodiment, the migraine symptom microcurrent has a nominal time-averaged current of 120 microamps.

According to an embodiment, the migraine treatment microcurrent has a peak current density where the treatment electrode contacts the user's skin of greater than 200 milliamps per square centimeter. According to an embodiment, the migraine treatment microcurrent has a peak current density where the treatment electrode contacts the user's skin of greater than 150 milliamps per square centimeter. According to an embodiment, the migraine treatment microcurrent has a peak current density less than 450 milliamps per square centimeter. According to an embodiment, the migraine treatment microcurrent has a nominal peak current density of about 300 milliamps per square centimeter.

According to an embodiment, the frequency of the treatment biphasic waveform microcurrent is less than 100 Hz. According to an embodiment, the frequency of the migraine treatment microcurrent is between 10 Hertz and 100 Hertz. According to an embodiment, the nominal frequency of the microcurrent is about 15 Hertz.

According to an embodiment, during the treatment mode, the handheld microcurrent migraine treatment device 102 measures the impedance by measuring the peaks of the treatment microcurrent. According to an embodiment, the handheld microcurrent migraine treatment device 102 adjusts a stimulation voltage applied between the treatment electrode 108 and the return electrode 110 to bring the magnitude of the peaks of the treatment microcurrent back to a desired constant value.

According to an embodiment, in the detection mode in which the handheld microcurrent migraine treatment device 102 identifies treatment locations, the handheld microcurrent migraine treatment device 102 measures the impedance by applying a detection current with a waveform similar or identical to the treatment microcurrent waveform and measuring the magnitude of the current peaks of the detection current in order to determine the impedance. According to an embodiment, the handheld microcurrent migraine treatment device 102 measures the impedance by passing a detection current with a smaller magnitude than the treatment microcurrent. According to an embodiment, during the detection mode, the handheld microcurrent migraine treatment device 102 applies a detection voltage that is lower than the stimulation voltage applied during the treatment mode. According to an embodiment, the handheld microcurrent migraine treatment device 102 measures the impedance by passing a detection current with a waveform different than the treatment microcurrent waveform.

In one embodiment, during the treatment mode, the handheld microcurrent migraine treatment device 102 measures the impedance by measuring the current spikes 750 or peaks of the treatment current. In one embodiment, the handheld microcurrent migraine treatment device 102 adjusts a stimulation voltage applied between the treatment electrode 108 and the return electrode 110 to bring the magnitude of the current spikes 750 or peaks of the treatment current back to a desired constant value.

Those of skill in the art will recognize, in light of the present disclosure, that in practice the treatment current may vary from the waveform 700. For example, the rise time and fall time of a given current spike 750 may not be identical. The rise times and fall times of separate current spikes 750 may not be identical to each other. A given current spike 750 may include, at the tail end, a brief portion that flows in the opposite polarity to the primary polarity of the current spike 750 (such as may be seen in a flyback effect). In a constant current situation, the current spikes 750 may have slightly differing magnitudes while remaining substantially the same. There may be noise present among the current waveform. All such variations from the waveform 700 fall within the scope of the present disclosure. It will be understood that the terms constant current and constant peak current are synonymous and comprehend such variations.

In one embodiment, the current spikes 750 are sharp increases in current followed by a sharp drop in current. In one embodiment, the rise time and fall time of a current spike 750 makes up 90% or more of the current spike 750.

FIG. 8 is a flowchart of a process 800 for operating a handheld microcurrent migraine treatment device, according to one embodiment. At 802, an electrical impedance is measured, during a detection mode of the handheld microcurrent migraine treatment device 102, between a treatment electrode 108 and a return electrode 110 of the handheld microcurrent migraine treatment device 102 as the treatment electrode 108 moves across the skin of a user and the return electrode 110 is in contact at a hand of the user, according to one embodiment.

At 804, a trigger condition is established, during the detection mode, based on the impedance, according to one embodiment.

At 806, a treatment mode of the handheld microcurrent migraine treatment device 102 is triggered when the trigger condition is met, the treatment mode including outputting a signal to the user that the microcurrent migraine treatment device has entered a treatment mode, according to one embodiment.

At 808, a therapeutic microcurrent is passed, during the treatment mode, between the treatment electrode 108 and the return electrode 110 through the skin of the user, according to one embodiment.

According to an embodiment, establishing the trigger condition includes calculating an average of a plurality of previously measured impedance values and calculating an impedance threshold as a selected percentage of the average. The trigger condition is the calculated impedance threshold.

FIG. 9 is a flowchart of a process 900 for operating a handheld microcurrent migraine treatment device, according to one embodiment. At 902, the handheld microcurrent migraine treatment device is turned on and enters a detection mode.

At 904, in the detection mode, while the user glides a treatment electrode across their skin in a template area for treating migraine symptoms, a detection circuit, also referred to as an adaptive trigger circuit, 106 (see FIG. 1) of the handheld microcurrent migraine treatment device determines a microcurrent treatment threshold and measures an electrical impedance between the treatment electrode 108 of the handheld microcurrent migraine treatment device 102 in contact with a sequence of points on a user's skin, through underlying tissues, through the user's arm and hand, and a return electrode 110 at the surface of the handheld microcurrent migraine treatment device 102 in contact with the user's hand to produce a detected impedance, according to one embodiment.

At 906, the detected impedance is compared to a dynamically determined treatment threshold, according to one embodiment.

At 908, a treatment mode is triggered if the detected impedance satisfies the treatment threshold. The treatment mode is not triggered if the detected impedance does not satisfy the treatment threshold. The therapeutic microcurrent is applied through the treatment electrode 108 and the present location of the user's skin, according to one embodiment. According to an embodiment, triggering of the treatment mode includes triggering an output of a treatment mode signal to the user that the microcurrent migraine symptom treatment device has exited the detection mode and entered the treatment mode. The user interprets the treatment mode signal as an indication that they should keep the treatment electrode still and in contact with the detected treatment location.

At 910, the treatment threshold is updated using the detected impedance, according to one embodiment.

According to an embodiment, a user grasps a microcurrent migraine treatment device, thereby making electrical contact between the user's hand and a return electrode positioned in the device housing. The user then positions the microcurrent migraine treatment device so as to bring a treatment electrode of the device into contact with the user's skin in a treatment region for treating migraine symptoms. The user maintains contact between the treatment electrode and the first skin surface location while the microcurrent migraine treatment device produces a voltage signal across the treatment electrode and the return electrode, resulting in a current flow between the electrodes and through a portion of the user's body. The current value depends upon the voltage applied across the electrodes and the impedance of the current path through the user's body. The impedance, in turn, depends upon the location at which the treatment electrode contacts the user's skin.

As the user moves the treatment electrode across the skin within the area for treating migraine symptoms, the microcurrent migraine treatment device detects the varying impedance, and compares the detected impedance with a threshold. When the user moves the treatment electrode to a treatment location within the area for treating migraine symptoms, the impedance drops below the threshold, the migraine treatment device detects the current drop, and triggers initiation of a treatment mode.

According to an embodiment, the voltage applied by the microcurrent migraine treatment device produces a current having a biphasic waveform, on the basis of which the device obtains periodic discrete impedance values. According to an embodiment, the microcurrent migraine treatment device continually updates the value of the threshold on the basis of a moving average, in which a plurality of recently detected impedance values are averaged and the threshold value is derived therefrom.

According to another embodiment, the microcurrent migraine treatment device determines a slope of change in impedances as they are detected, and derives the threshold at least in part on the slope, or on a moving average of slope values.

According to an embodiment, the microcurrent migraine treatment device produces a signal to the user when a treatment mode is initiated. The signal may be produced, for example, by illumination of LEDs located in a housing of the device, or by a haptic signal produced by the device.

According to an embodiment, upon receipt of the signal indicating initiation of the treatment mode, the user holds the treatment electrode in the treatment location for a predetermined treatment period. At the end of the treatment period, microcurrent migraine treatment device signals that the treatment period has expired, and the user resumes movement of the treatment electrode over the skin until the device signals detection of another treatment location M, whereupon a new treatment mode is initiated.

According to an embodiment, the microcurrent migraine device applies the biphasic waveform for a duration of between 5 seconds and 30 seconds before outputting a signal that the treatment period has expired.

According to an embodiment, the microcurrent migraine device signals that the treatment period stopping outputting a light signal or stopping outputting a haptic signal, or both.

According to an embodiment, the term template refers to a treatment region of the user's skin within which a plurality of treatment locations M for treating migraine are located. According to an embodiment, the treatment location Ms are located superjacent to the occipital nerve, auricular nerve, and/or cervical nerves, and are detectable on the basis of lower impedance values at those locations, as compared with impedances at surrounding locations.

The term "template" refers to a set of preplanned treatment locations corresponding to nominal nerve locations. For example, a sampling or all of the locations identified as "M" in FIG. 3 may act as a template for treatment locations.

According to an embodiment, in response to variations in impedance the microcurrent migraine treatment device varies the voltage across the electrodes, in order to maintain a substantially constant current.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A method for applying a therapeutic microcurrent for treatment of migraine, comprising:

measuring an electrical impedance between a treatment electrode of a handheld microcurrent migraine treatment device in contact with a user's skin superjacent a treatment location over a trigeminal nerve, occipital nerve, cervical nerve, or auricular nerve and a return electrode at the surface of the handheld microcurrent migraine treatment device in contact with the user's hand to produce a detected impedance;

comparing the detected impedance to a dynamically determined treatment threshold;

triggering a treatment mode by outputting a treatment indicator to the user if the detected impedance satisfies the treatment threshold and not outputting a treatment indicator to the user if the detected impedance does not satisfy the treatment threshold;

applying a treatment microcurrent having a peak microcurrent density of less than 250 milliamps per square centimeter at the skin surface and through the trigeminal nerve, occipital nerve, cervical nerve, or auricular nerve; and updating the treatment threshold using the detected impedance.

2. The method of claim 1, wherein the detected impedance is produced from the measured electrical impedance by performing an analog-to-digital conversion on the detected impedance.

3. The method of claim 1, wherein satisfaction of the impedance threshold includes the detected impedance having a value equal to or less than the dynamically determined impedance threshold.

4. The method of claim 1, wherein converting the detected impedance to a detected impedance includes determining a first derivative of the detected impedance.

5. The method of claim 1, wherein the microcurrent passes from the treatment electrode to the return electrode through the user's body including a portion of the user's head, neck, arm, and hand;

whereby tissues subjacent to the treatment electrode are exposed to a therapeutic waveform produced by the handheld microcurrent migraine treatment device.

6. The method of claim 1, wherein the microcurrent passes from the return electrode to the treatment electrode through the user's body including the user's hand, arm, neck, and a portion of the user's head;

whereby tissues subjacent to the treatment electrode are exposed to a therapeutic waveform produced by the handheld microcurrent migraine treatment device.

7. The method of claim 1, further comprising alternating a polarity of the microcurrent during application of the microcurrent.

8. The method of claim 1, wherein outputting a treatment indicator to the user if the detected impedance satisfies the treatment threshold includes outputting a haptic feedback of the handheld microcurrent migraine treatment device during application of the microcurrent.

9. The method of claim 1, wherein outputting a treatment indicator to the user if the detected impedance satisfies the treatment threshold includes illuminating a light emitting diode of the handheld microcurrent migraine treatment device during application of the microcurrent.

10. The method of claim 1, wherein the return electrode is coextensive with at least a portion of a housing of the handheld microcurrent migraine treatment device, and wherein the return electrode is exposed to contact the hand of the user.

11. The method of claim 1, further comprising turning off the handheld microcurrent migraine treatment device when the impedance between the treatment electrode and the return electrode is greater than a pre-determined threshold for a pre-determined time period.

12. The method of claim 1, wherein the return electrode includes a conductive housing of the handheld microcurrent migraine treatment device.

13. The method of claim 12, wherein the housing includes conductive polycarbonate.

14. The method of claim 12, wherein the treatment electrode includes at least one of gold, silver, stainless steel, carbon fiber, titanium, and alternating bond length organic polymer.

15. The method of claim 1, further comprising:

outputting a therapeutic microcurrent including a biphasic alternating polarity waveform having a frequency less than 100 Hz.

16. The method of claim 1, wherein the biphasic waveform has a frequency of about 15 Hertz.

17. The method of claim 1, further comprising:

outputting a therapeutic microcurrent including biphasic, alternating polarity waveform having a time-averaged value of between 60 and 300 microamps.

18. The method of claim 1, wherein the peak microcurrent is about 6 milliamps.

19. A method for applying a therapeutic microcurrent for treatment of migraine, comprising:

measuring an electrical impedance between a treatment electrode of a handheld microcurrent migraine treatment device in contact with a user's skin superjacent a treatment location over a trigeminal nerve, occipital nerve, cervical nerve, or auricular nerve and a return electrode at the surface of the handheld microcurrent migraine treatment device in contact with the user's hand to produce a detected impedance;

comparing the detected impedance to a dynamically determined treatment threshold;

triggering a treatment mode by outputting a treatment indicator to the user if the detected impedance satisfies the treatment threshold and not outputting a treatment indicator to the user if the detected impedance does not satisfy the treatment threshold;

applying a treatment microcurrent having a peak microcurrent density of less than 250 milliamps per square centimeter at the skin surface and through the trigeminal nerve, occipital nerve, cervical nerve, or auricular nerve; and updating the treatment threshold using the detected impedance;

wherein the peak microcurrent density is greater than 50 milliamps per square centimeter at the skin surface.

20. The method of claim 19, wherein the peak microcurrent density is about 100 milliamps per square centimeter at the skin surface.

21. The method of claim 1, wherein outputting the treatment current includes outputting a therapeutic microcurrent including a biphasic, alternating polarity waveform, wherein the biphasic waveform has a duty cycle of less than 5%.

22. The method of claim 21, wherein the biphasic waveform has a duty cycle of about 2%.

23. The method of claim 1, further comprising:

outputting a therapeutic microcurrent including biphasic, alternating polarity waveform, wherein the average microcurrent is less than 300 microamps.

24. The method of claim 1, wherein the biphasic waveform has an average current of greater than 60 microamps.

25. The method of claim 1, wherein the biphasic waveform has an average current of about 120 microamps.

26. The method of claim 1, further comprising generating the dynamically determined impedance threshold as a selected percentage of an average impedance of a plurality of previously detected impedance values.

\* \* \* \* \*